United States Patent
Seo et al.

(10) Patent No.: US 12,027,031 B2
(45) Date of Patent: Jul. 2, 2024

(54) WEARABLE DEVICE, SYSTEM INCLUDING ELECTRONIC DEVICE AND WEARABLE DEVICE, AND METHOD

(71) Applicant: Samsung Electronics Co., Ltd., Gyeonggi-do (KR)

(72) Inventors: Hyejung Seo, Gyeonggi-do (KR); Hyuncheol Park, Gyeonggi-do (KR); Jinhee Won, Gyeonggi-do (KR); Seongmin Je, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 203 days.

(21) Appl. No.: 17/555,623

(22) Filed: Dec. 20, 2021

(65) Prior Publication Data

US 2022/0198903 A1 Jun. 23, 2022

Related U.S. Application Data

(63) Continuation of application No. PCT/KR2021/018162, filed on Dec. 2, 2021.

(30) Foreign Application Priority Data

Dec. 23, 2020 (KR) .................. 10-2020-0182001

(51) Int. Cl.
*G08B 21/14* (2006.01)
*A61B 5/00* (2006.01)
(Continued)

(52) U.S. Cl.
CPC ............ *G08B 21/14* (2013.01); *A61B 5/1112* (2013.01); *A61B 5/742* (2013.01); *A61B 5/746* (2013.01);
(Continued)

(58) Field of Classification Search
CPC ....... G08B 21/14; A61B 5/1112; A61B 5/742; A61B 5/746; A61B 5/14551; A61B 5/14542; G01N 33/0063; G04G 21/025
See application file for complete search history.

(56) References Cited

U.S. PATENT DOCUMENTS 8,690,769 B2 4/2014 Edman et al.
9,311,805 B2* 4/2016 Zishaan ................. G08B 25/10
(Continued)

FOREIGN PATENT DOCUMENTS

JP 4589341 B2 9/2010
JP 2022-80503 A 5/2022
(Continued)

OTHER PUBLICATIONS

International Search Report dated Mar. 31, 2022.

*Primary Examiner* — Daniell L Negron
(74) *Attorney, Agent, or Firm* — Cha & Reiter, LLC

(57) ABSTRACT

A wearable electronic device and method are disclosed, including a display, a biometric sensor, a communication circuitry, and a processor. The processor implements the method, including: receiving a transmission including air quality information from an external electronic device equipped with a gas sensor, detecting, via a biometric sensor, biometric information of a user, identifying, via at least one processor, a dangerous situation based at least partly on the air quality information and the biometric information, and displaying a notification message indicating the identified dangerous situation through at least one of a display of the wearable electronic device, or the external electronic device, based on the identification of the dangerous situation.

13 Claims, 12 Drawing Sheets

(51) Int. Cl.
*A61B 5/11* (2006.01)
*G01N 33/00* (2006.01)
*G04G 21/02* (2010.01)
*A61B 5/1455* (2006.01)

(52) U.S. Cl.
CPC ....... *G01N 33/0063* (2013.01); *G04G 21/025* (2013.01); *A61B 5/14551* (2013.01)

(56) References Cited

U.S. PATENT DOCUMENTS

| | | | |
|---|---|---|---|
| 10,371,682 B2 * | 8/2019 | Berndt | G01N 33/0073 |
| 10,627,381 B2 * | 4/2020 | Kim | A61B 5/369 |
| 11,524,187 B1 * | 12/2022 | Dashevsky | G16H 50/30 |
| 2009/0030289 A1 | 1/2009 | Katayama et al. | |
| 2010/0217096 A1 | 8/2010 | Nanikashvili | |
| 2015/0145686 A1 * | 5/2015 | Johnson, Jr. | G01N 33/0006 340/632 |

FOREIGN PATENT DOCUMENTS

| | | | | |
|---|---|---|---|---|
| KR | 10-2016-0074435 A | 6/2016 | | |
| KR | 10-2017-0025479 A | 3/2017 | | |
| KR | 10-2017-0101385 A | 9/2017 | | |
| KR | 10-1814335 B1 | 12/2017 | | |
| KR | 10-2019-0031071 A | 3/2019 | | |
| KR | 10-1962002 B1 | 3/2019 | | |
| KR | 10-2133180 B1 | 7/2020 | | |
| KR | 10-2152738 B1 | 9/2020 | | |
| KR | 10-2189049 B1 | 12/2020 | | |
| KR | 102189049 B1 * | 12/2020 | ............ | G01N 15/02 |
| KR | 10-2347708 B1 | 1/2022 | | |

\* cited by examiner

WEARABLE DEVICE, SYSTEM INCLUDING ELECTRONIC DEVICE AND WEARABLE DEVICE, AND METHOD

CROSS-REFERENCE TO RELATED APPLICATION(S)

This application is a continuation of International Application No. PCT/KR2021/018162, filed on Dec. 2, 2021, which claims priority to Korean Patent Application No. 10-2020-0182001 filed on Dec. 23, 2020, in the Korean Intellectual Property Office, the disclosures of which are herein incorporated by reference.

TECHNICAL FIELD

The present disclosure relates to a wearable device configured to monitor air quality information and user biometric information, a system including an electronic device and the wearable device, and a method.

BACKGROUND ART

Recently, wearable devices that can be worn on the human body have been developed. For example, a watch-type smart device is worn on the user's wrist, an earbud-type smart device is worn on the user's ear, and a smart glass-type device is worn on the user's head. The wearable device may enable unique control interactions and/or display environments for the user.

The wearable device may monitor the user biometric signals. For example, the wearable device may measure a bio-signal such as heart rate, pulse rate, blood oxygen saturation, blood pressure, or blood sugar. As such, the biometric information obtained by the wearable device may include information related to the user's health.

Despite the ability to capture the user's biometric information, the user's biometric information alone cannot account for environmental causes that affect the user's health.

SUMMARY

The present disclosure is directed to providing a wearable device capable of providing a guide to health and safety of a user by linking air quality information obtained by a separate electronic device to user biometric information obtained by a local device, a system including the electronic device and the wearable device, and a method.

In an embodiment of the present disclosure, a wearable electronic device is disclosed, including a display, a biometric sensor configured to detect biometric information, a communication circuitry configured to communicate with an external electronic device equipped with a gas sensor, and a processor, configured to identify a dangerous situation based on the detected biometric information and air quality information received from the electronic device through the communication circuitry, and control the display to display a guide message (also, called notification message) indicating the dangerous situation.

The processor may be configured to determine a content of the guide message based on a concentration of harmful gas contained in the air quality information and a blood oxygen saturation level contained in the biometric information.

The processor may be configured to control the display to display the guide message by applying a user's exposure time to the harmful gas.

The communication circuitry may be configured to communicate with a server, and the processor may be configured to control the communication circuitry to receive a plurality of pieces of air quality information obtained by a plurality of electronic devices from the server, and configured to determine the concentration of the harmful gas by applying a weight to each of the plurality of pieces of air quality information.

The processor may be configured to determine the weight based on a sensitivity constant of each of the plurality of electronic devices.

The wearable device may further include a distance sensor configured to obtain distance data to the electronic device, and the processor may be configured to determine a distance to the electronic device based on at least one of the distance data or a signal strength of the electronic device, configured to estimate a concentration of the harmful gas at a user's location based on the distance to the electronic device, and configured to determine a content of the guide message based on the estimated concentration of harmful gas and the blood oxygen saturation level.

The communication circuitry may further include a Global Positioning System (GPS) receiver configured to obtain location information, and the processor may be configured to determine a distance to the electronic device based on the location information.

The processor may be configured to control the biosensor to obtain the biometric information in response to a request for obtaining the biometric information received from the electronic device.

The communication circuitry may be configured to communicate with a server, and the processor may be configured to control the communication circuitry to transmit a sharing request, which is for sharing the guide message regarding the dangerous situation with an external device, to the server.

Another aspect of the present disclosure provides a method including receiving, via communication circuitry, a transmission including air quality information from an external electronic device equipped with a gas sensor, detecting, via a biometric sensor, biometric information of a user, identifying, via at least one processor, a dangerous situation based at least partly on the air quality information and the biometric information, and displaying a a guide message (also, called notification message) indicating the identified dangerous situation through at least one of a display of the wearable electronic device, or the external electronic device, based on the identification of the dangerous situation.

The displaying of the guide message may include determining a content of the guide message based on a concentration of harmful gas contained in the air quality information and a blood oxygen saturation level contained in the biometric information.

The displaying of the guide message may be performed by further consideration of a user's exposure time to the harmful gas.

The obtaining of the air quality information may include obtaining a plurality of pieces of air quality information obtained by a plurality of electronic devices from a server, and determining the concentration of the harmful gas by applying a weight to each of the plurality of pieces of air quality information.

The determination of the concentration of the harmful gas may include determining the weight based on a sensitivity constant of each of the plurality of electronic devices.

The determination of the dangerous situation may include determining a distance between the electronic device and the wearable device and estimating a concentration of the harmful gas at a user's location based on the distance between the electronic device and the wearable device, and the determination of the content of the guide message may include determining the content of the guide message based on the estimated concentration of harmful gas and the blood oxygen saturation level.

The determination of the distance may be performed based on at least one of distance data to the electronic device obtained by a distance sensor of the wearable device or a signal strength of the electronic device received by the wearable device.

The determination of the distance may be performed based on location information obtained by a Global Positioning System (GPS) receiver.

The method may further include requesting, by the electronic device, the wearable device to obtain the biometric information in response to the concentration of the harmful gas contained in the air quality information being greater than or equal to a predetermined value.

The method may further include transmitting a sharing request, which is for sharing the guide message regarding the dangerous situation with an external device, to a server.

Another aspect of the present disclosure provides a system including an electronic device including a gas sensor and configured to obtain air quality information, and a wearable device configured to obtain user biometric information. At least one of the electronic device or the wearable device is configured to determine a dangerous situation based on a concentration of harmful gas contained in the air quality information and a blood oxygen saturation level contained in the biometric information, and configured to display a guide message regarding the dangerous situation.

It is possible to provide electronic guidance to health and safety of a user by linking air quality information obtained by a separate electronic device to user biometric information detected by the local device.

Further, by monitoring air quality information at a location of the electronic device, and user biometric information, it is possible to properly notify a user dangers that may occur due to changes in external environment.

DETAILED DESCRIPTION

Hereinafter certain embodiments of the present disclosure will be described with reference to the accompanying drawings. However, this is not intended to limit the present disclosure to specific embodiments, and it should be understood that various modifications, equivalents, and/or alternatives of the embodiments of the present disclosure are included.

Figure 1:
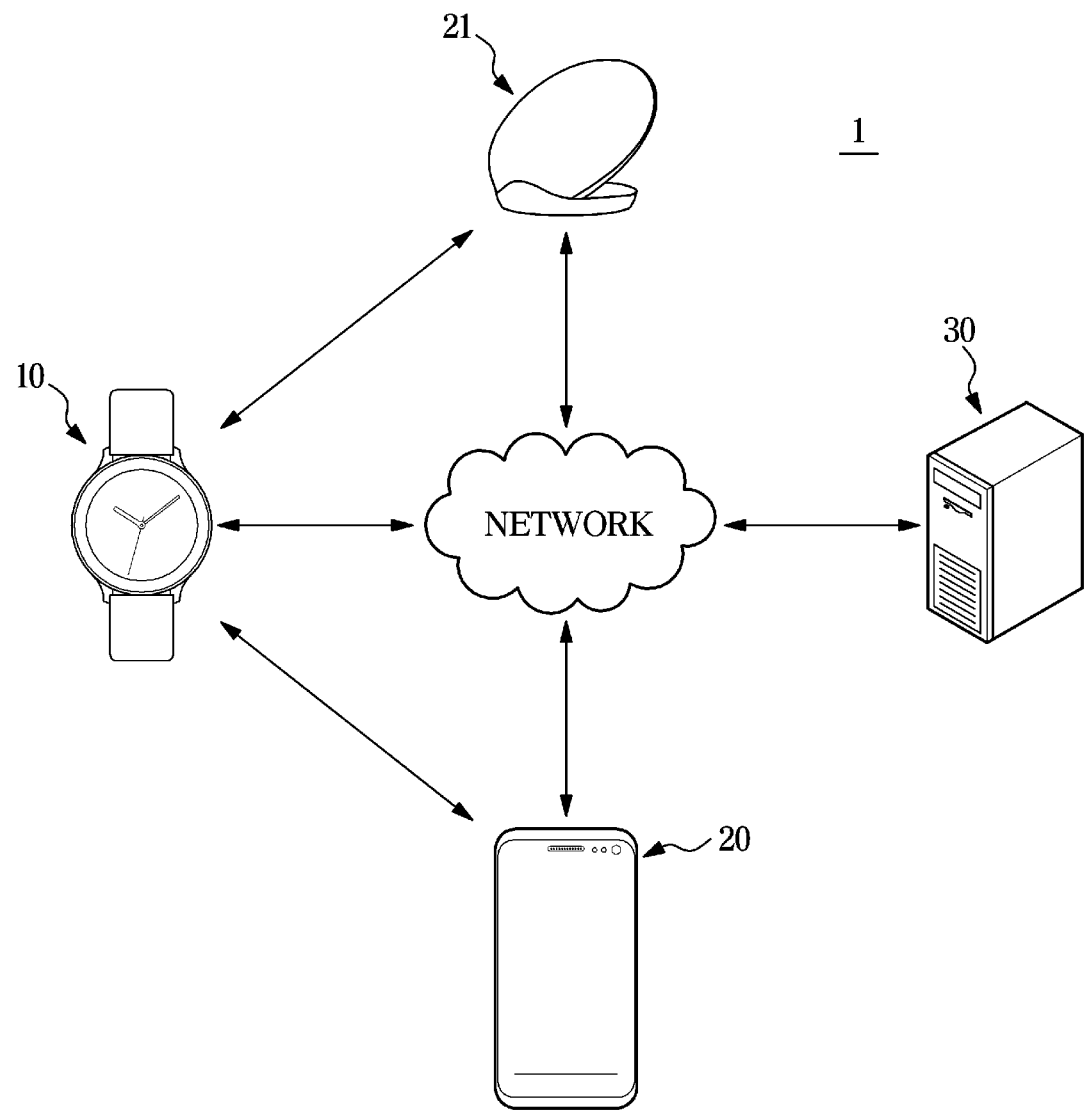
FIG. 1 illustrates a system including a wearable device and an electronic device according to an embodiment of the present disclosure.

FIG. 1 illustrates a system including a wearable device and an electronic device according to an embodiment of the present disclosure.

Referring to FIG. 1, a system 1 according to an embodiment may include a wearable electronic device 10 (i.e., "wearable device") and at least one electronic device 20 and 21. The system 1 may further include a server 30. The wearable device 10 may be worn or attached to the user's body to obtain biometric information. The wearable device 10 may be implemented in various forms, such as clothes, shoes, gloves, glasses, a hat, or accessories, and may be exemplified as a smart watch as shown in FIG. 1. The electronic devices 20 and 21 may include various types of devices. For example, the electronic devices 20 and 21 may include devices such as a smartphone, a wireless charger, a speaker, an earbud cradle, an Internet of Things (IoT) device, a computer, or a tablet, which are operable as an air measuring device. A first electronic device 20 may be exemplified as a smartphone, and a second electronic device 21 may be exemplified as a wireless charger.

The wearable device 10 may be communicatively connected to the electronic devices 20 and 21. The wearable device 10 may communicate with the electronic devices 20 and 21 through a short-range wireless communication network. The wearable device 10 may communicate with the electronic devices 20 and 21 or the server 30 through a long-distance wireless communication network. Transmission or reception of data may be performed between the wearable device 10 and the electronic devices 20 and 21 through the server 30. For example, the wearable device 10 may be connected to at least one of the electronic devices 20 and 21 or the server 30 through a communication technology such as Bluetooth, Wi-Fi, Radio Frequency (RF) communication, infrared communication, Ultra-Wide Band (UWB) communication, Near Field Communication (NFC), Zigbee, cellular communication, or wide area network (WAN). In addition, various communication technologies may be applied thereto.

Figure 2:
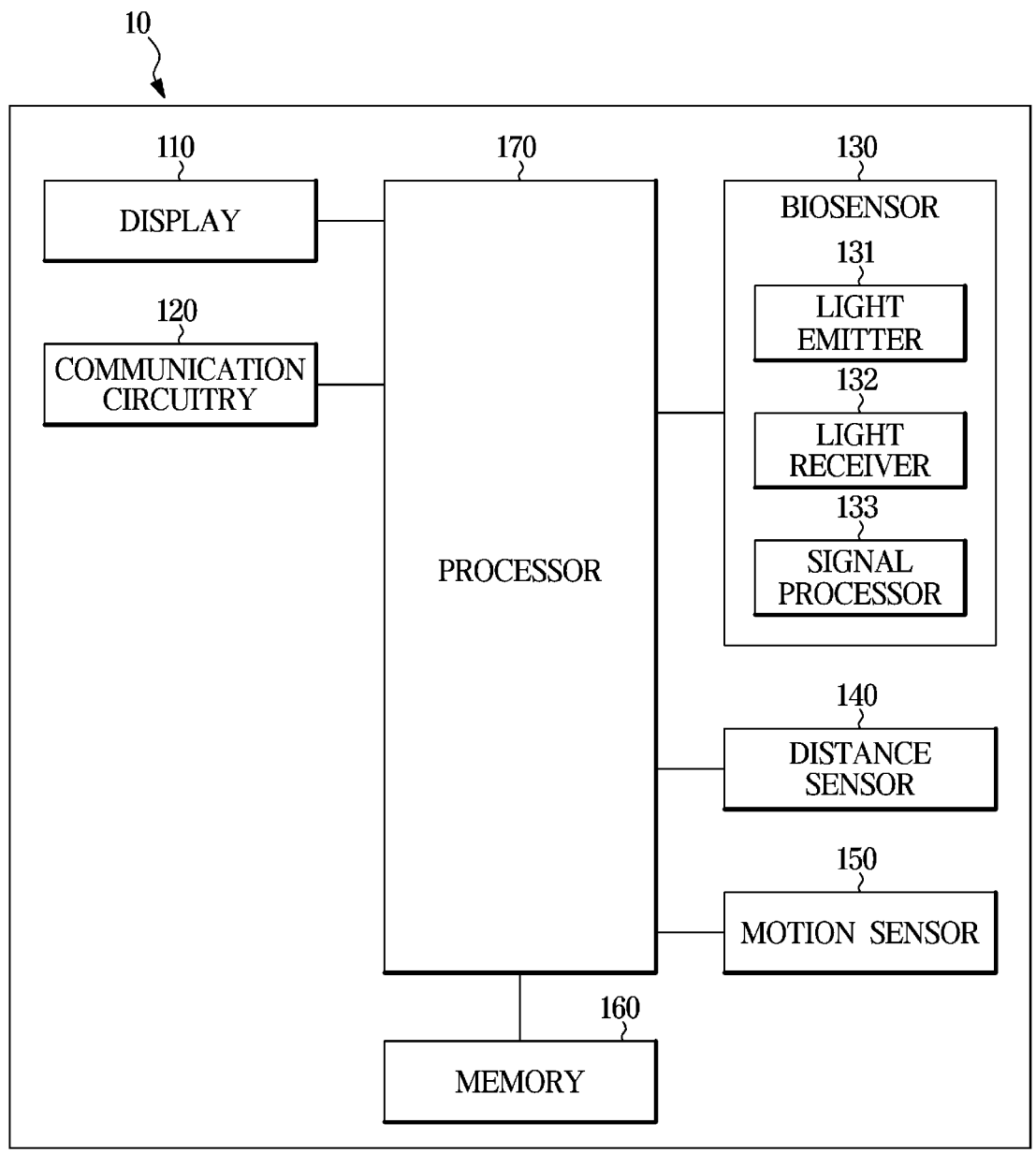
FIG. 2 is a block diagram of the wearable device according to an embodiment of the present disclosure.

FIG. 2 is a block diagram of the wearable device according to an embodiment of the present disclosure.

Referring to FIG. 2, the wearable device 10 may include a display 110, a communication circuitry 120, a biosensor 130 (i.e., a biometric sensor), a memory 160, and a processor 170. The wearable device 10 may further include a distance sensor 140 and a motion sensor 150. The processor 170 may be electrically connected to components of the wearable device 10 and may control each component.

The display 110 may provide visual information to the outside (e.g., a user) of the wearable device 10. For example, the display 110 may output at least one piece of biometric information, air quality information, and a guide message related to a dangerous situation. The display 110 may be implemented as a liquid crystal display (LCD), an organic light emitting display (OLED), a quantum dot LED, a mini LED, or a micro LED. The display 110 may include a touch sensor configured to sense a touch or a pressure sensor configured to measure an intensity of a force generated by the touch.

The communication circuitry 120 may establish a communication channel with at least one of the electronic device 20 or the server 30, and may support transmission and reception of data through the established communication channel. The communication circuitry 120 may be implemented using various communication technologies configured to support wired communication or wireless communication. For example, a communication technology such as Bluetooth, Wi-Fi, RF communication, infrared communication, UWB communication, NFC, Zigbee, cellular communication, or WAN may be applied to the communication circuitry 120. In addition, the communication circuitry 120 may further include a Global Positioning System (GPS) receiver configured to obtain location information.

The biosensor 130 may obtain the user biometric information and convert the biometric information into digital data. The biosensor 130 may be arranged on a surface of the wearable device 10 adjacent to the user. The biosensor 130 may transmit the biometric information to the processor 170. The biometric information may include at least one of blood oxygen saturation level, heart rate, pulse rate, blood pressure, blood sugar, and skin tone.

The processor 170 may control the biosensor 130 to periodically obtain biometric information, obtain biometric information based on a user input, or obtain biometric information in response to a request for obtaining biometric information received from the electronic device 20 or the server 30.

The biosensor 130 (i.e., biometric sensor) may correspond to an optical sensor and may include a light emitter 131, a light receiver 132, and a signal processor 133. The light emitter 131 may include a light emitting diode (LED) configured to emit light of various wavelengths. For example, the light emitter 131 may allow at least one of the plurality of light emitting elements, which is configured to emit light corresponding to each of a red wavelength (600 nm to 700 nm), a green wavelength (500 nm to 600 nm), a blue wavelength (400 nm to 500 nm), or an infrared wavelength (780 nm to 1000 nm), to be output sequentially or simultaneously. In addition, the light emitter 131 may include at least one of a spectrometer (i.e., spectrography), a vertical cavity surface emitting laser (VCSEL), an LED, a white LED, and a white laser, which are configured to control a wavelength.

For example, a green wavelength is a wavelength generally used for heart rate measurement, and a red wavelength may also penetrate relatively deeply into the user's skin to be used for heart rate measurement. The blue wavelength may be used to measure blood sugar. The infrared wavelength may be used together with the red wavelength to measure blood oxygen saturation level. In addition, a red wavelength, a green wavelength, and an infrared wavelength may be used together for skin tone measurement. As light of various wavelengths is used, more biometric information may be obtained. The biosensor 130 may be operated to obtain at least two or more pieces of biometric information among the plurality of pieces of biometric information such as a pulse, blood oxygen saturation level, and blood pressure. For example, the biosensor 130 may be operated to simultaneously obtain a pulse, blood oxygen saturation level, and blood pressure.

The light receiver 132 may include a detector configured to detect light. For example, the light receiver 132 may detect at least a portion of light (light signal) that is reflected by the user's body tissue (e.g., skin, skin tissue, fat layer, vein, artery, and/or capillary), among light output from the light emitter 131. The light receiver 132 may output a current signal having a magnitude corresponding to the detected intensity of light. The light receiver 132 may include a plurality of detectors to detect light of a plurality of wavelengths. For example, the light receiver 132 may detect at least one of red light, green light, blue light, and infrared light. For example, the light receiver 132 may include at least one an avalanche photodiode (APD), a single photon detection avalanche diode (SPAD), a photodiode, a photomultiplier tube (PMT), a charge coupled device (CCD), a CMOS array, and a spectrometer. In an embodiment, a structure of the at least one light receiver 132 may be a reflective type or a transmissive type. However, the configuration included in the biosensor 130 is not limited to the light emitter 131 and the light receiver 132.

The signal processor 133 may control the light emitter 131 and the light receiver 132 under the control of the processor 170. The signal processor 133 may drive the light emitter 131 and may process a signal output by the light receiver 132. For example, the signal processor 133 may convert a current signal output by the light receiver 132 into a voltage signal, amplify and filter the voltage signal, and convert the voltage signal into a digital signal. The signal processor 133 (e.g., an analog front end) may include an amplifier configured to amplify a bio-signal, and an analog to digital converter (ADC) configured to convert an analog bio-signal into a digital bio-signal. However, a configuration included in the signal processor 133 is not limited to the above-described amplifier and ADC. Although it has been described that the signal processor 133 is included in the biosensor 130, the present disclosure is not limited thereto. Alternatively, the signal processor 133 may be included in the processor 170.

Further, the biosensor 130 may further include at least one of an electrocardiogram (ECG) sensor, a galvanic skin response (GSR) sensor, an electroencephalogram (EEG) sensor, a bioelectrical impedance analysis (BIA) sensor, or a bioimpedance sensor. The biosensor 130 may include a laser diode (LD) and an image sensor.

The distance sensor 140 may obtain distance data to an external object (e.g., the electronic device 20). The distance sensor 140 may be a time of flight (TOF) sensor. The distance sensor 140 may emit infrared light, receive light reflected from an object, and obtain distance data related to a distance to the object, based on a reception time of the reflected light. The distance sensor 140 may obtain 3D depth information. Further, the distance sensor 140 may be implemented as an ultrasonic sensor or a laser sensor.

The motion sensor 150 may include at least one of a gesture sensor, a gyro sensor, an acceleration sensor, and a proximity sensor. The motion sensor 150 may obtain user's motion data. In addition, the wearable device 10 may include various sensors. For example, the wearable device 10 may include at least one of an air pressure sensor, a magnetic sensor, a grip sensor, a color sensor, a temperature sensor, a humidity sensor, and an illuminance sensor.

The memory 160 may store various data used by at least one component (e.g., the biosensor 130 and the processor 170) of the wearable device 10. Data may include software, programs, input data, and output data. The memory 160 may include at least one of a volatile memory and a non-volatile memory. The program may be stored as software in the memory 160 and may include an operating system, a middleware, or an application.

For example, the memory 160 may store biometric information obtained by the biosensor 130 and air quality information transmitted from the electronic device 20. Further, the memory 160 may store personal information including the user's age, height, and/or weight.

The processor 170 may execute software or a program stored in the memory 160 to control components of the wearable device 10, and may perform data processing or data operation. The processor 170 may store result data by data processing or data operation in the memory 160. The processor 170 may include a central processing unit or an application processor. For example, the processor 170 may process the biometric information obtained by the biosensor 130 and the air quality information transmitted from the electronic device 20.

The processor 170 may determine a user state based on the biometric information. The user state may be divided into a normal state and an abnormal state, and the abnormal state may be subdivided into a caution state and a dangerous state. For example, in response to the heart rate or pulse rate obtained by the biosensor 130 exceeding a predetermined normal heart rate or in response to the blood oxygen saturation level being less than a predetermined normal saturation level, the processor 170 may determine the user state as an abnormal state. The processor 170 may control the display 110 to warn that the user state is the abnormal state.

The processor 170 of the wearable device 10 may determine a dangerous situation based on the air quality information and the biometric information, and may control the display 110 to provide a guide message regarding the dangerous situation according to the determination result.

Meanwhile, the wearable device 10 may further include various components. For example, the wearable device 10 may include an input device such as a microphone, a button, a sound output device, such as a speaker, a camera, and a battery.

Figure 3:
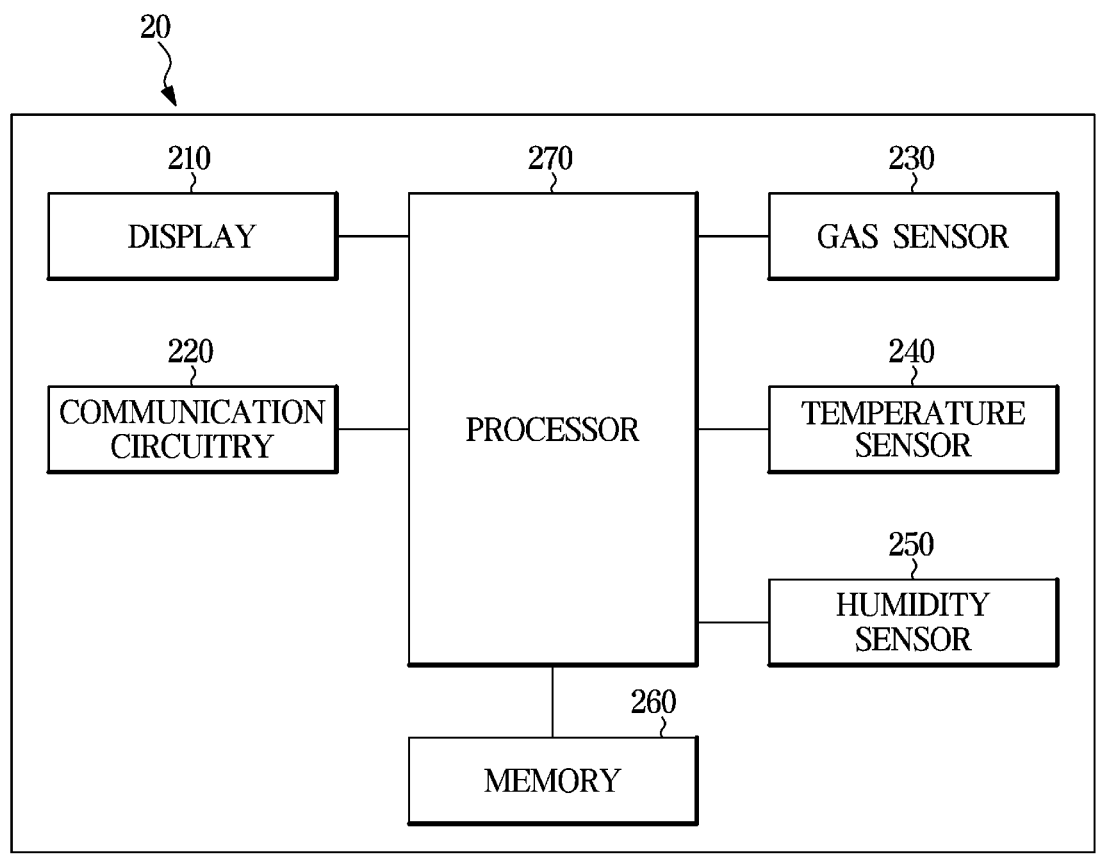
FIG. 3 is a block diagram of the electronic device according to an embodiment of the present disclosure.

FIG. 3 is a block diagram of the electronic device according to an embodiment of the present disclosure.

The electronic device 20 described in FIG. 1 may include the components of FIG. 3. Further, other electronic devices 21 may include the same components. Referring to FIG. 3, the electronic device 20 may include a display 210, a communication circuitry 220, a gas sensor 230, a memory 260, and a processor 270. The electronic device 20 may further include a temperature sensor 240 and a humidity sensor 250.

The display 210 of the electronic device 20 may display visual information. For example, the display 210 may display at least one piece of biometric information, air quality information, or a guide message related to the dangerous situation. The display 210 may be implemented as a liquid crystal display (LCD), an organic light emitting display (OLED), a quantum dot LED, a mini LED, or a micro LED. Further, the display 210 may include a touch screen.

The communication circuitry 220 may establish a communication channel with at least one of the wearable device 10 and the server 30, and may support transmission and reception of data through the established communication channel. The communication circuitry 220 may be implemented using various communication technologies configured to support the above-mentioned wired communication or wireless communication.

The gas sensor 230 may measure a concentration of the harmful gas. In other words, the gas sensor 230 may detect gas included in the air and measure the concentration of the detected gas. For example, the gas sensor 230 may measure the concentration of the harmful gas such as carbon monoxide, carbon dioxide, and total volatile organic compounds. The gas sensor 230 may include at least one of a semiconductor sensor, a ceramic humidity sensor, a piezoelectric sensor, a catalytic combustion sensor, a solid electrolyte sensor, an electrochemical sensor, and an infrared absorption sensor. The electronic device 20 may further include a fine dust sensor configured to measure fine dust, in addition to the gas sensor 230.

Meanwhile, when the plurality of electronic devices 20 and 21 including the gas sensor 230 is provided, air quality information obtained by the plurality of electronic devices 20 and 21 may be transmitted to the server 30. At least one of the wearable device 10, the electronic device 20, and the server 30 may determine the concentration of the harmful gas by applying a weight to a plurality of pieces of air quality information. A method of determining the concentration of harmful gas using the plurality of pieces of air quality information is described in detail with reference to FIG. 11.

The temperature sensor 240 may generate temperature data by measuring a temperature of a space in which the electronic device 20 is located. The humidity sensor 250 may generate humidity data by measuring humidity of a space in which the electronic device 20 is located.

The air quality information obtained by the electronic device 20 may include concentration data of harmful gas, and may further include temperature data and humidity data. Further, the air quality information may be transmitted to at least one of the wearable device 10 or the server 30.

The memory 260 may store software, programs, applications, instructions, and data for controlling the operation of the electronic device 20. For example, the memory 260 may store air quality information obtained by the gas sensor 230. The memory 260 may store temperature data obtained by the temperature sensor 240 and humidity data obtained by the humidity sensor 250. Further, the memory 260 may store the biometric information transmitted from the wearable device 10.

The processor 270 may execute software or a program stored in the memory 260 to control components of the electronic device 20, and may perform data processing or data operation. The processor 270 may store result data by data processing or data operation, in the memory 260.

The processor 270 of the electronic device 20 may control the gas sensor 230 to obtain air quality information at a predetermined interval. In addition, the processor 270 may control the gas sensor 230 to obtain air information in response to a request for obtaining air quality information transmitted from the wearable device 10 or the server 30. For example, when fire event information is transmitted from another electronic device 21, the server 30 may request the electronic device 20 to obtain air quality information.

The processor 270 of the electronic device 20 may process the air quality information to determine a user risk level corresponding to the air quality. The electronic device 20 may receive information on the user risk level corresponding to the air quality information from the wearable device 10 or the server 30. Further, the processor 270 of the electronic device 20 may control the communication circuitry 220 to transmit a signal for requesting for obtaining of biometric information to the wearable device 10. For example, in response to the concentration of the harmful gas included in the air quality information exceeding a predetermined threshold value, the electronic device 20 may request the wearable device 10 to obtain the biometric information. The wearable device 10 may control the biosensor 130 to obtain biometric information in response to the request for obtaining biometric information received from the electronic device 20. In response to determining that the measured air quality is bad (e.g., when the air quality measurement value is low), the electronic device 20 may request the wearable device 10 to obtain biometric information at a shorter interval.

The processor 270 of the electronic device 20 may determine the dangerous situation based on the air quality information and the biometric information transmitted from the wearable device 10, and may control the display 210 to provide a guide message regarding the dangerous situation according to the determination result.

Meanwhile, the electronic device 20 may further include various components. For example, the electronic device 20 may include an input device such as a microphone and a button, a sound output device such as a speaker, a camera, and a battery.

Figure 4:
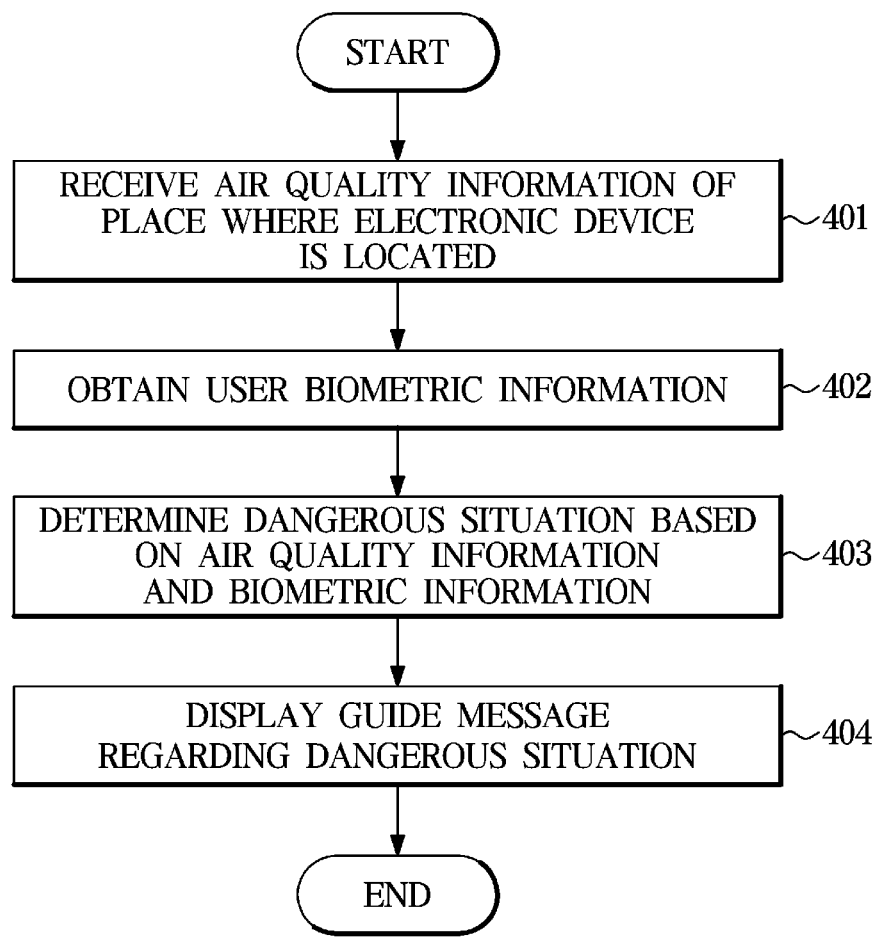
FIG. 4 is a flowchart illustrating a method of controlling the wearable device according to an embodiment of the present disclosure.

FIG. 4 is a flowchart illustrating a method of controlling the wearable device according to an embodiment of the present disclosure.

Referring to FIG. 4, the processor 170 of the wearable device 10 may control the communication circuitry 120 to receive air quality information regarding a location in which the electronic device 20 is located (401). The air quality information may include the concentration of a harmful gas or gasses contained in the air. For example, the air quality information may include a concentration carbon monoxide (CO), carbon dioxide (CO2), and total volatile organic compounds (TVOC). Thus, by receiving the air quality information from the electronic device 20 including the gas sensor 230, the air quality information may be provided.

The processor 170 of the wearable device 10 may control the biosensor 130 to obtain the user biometric information (402). The processor 170 may determine the user's state based on the biometric information. The user biometric information may include at least one of blood oxygen saturation level, heart rate, pulse rate, blood pressure, blood sugar, and skin tone. Particularly, blood oxygen saturation level (SpO2) means blood oxygen concentration and may be an important indicator of a user's health status. Blood oxygen saturation level may be directly affected by the air quality.

The processor 170 of the wearable device 10 may determine (e.g., detect) a present dangerous situation based on the air quality information and the biometric information (403) and may control the display 110 to display a guide message regarding the dangerous situation (404). For example, the processor 170 may determine the dangerous situation based on the concentration of harmful gas indicated in the air quality information (e.g., the presence of a dangerous gas above a predetermined threshold, expressed as parts-per-million "ppm" or percent concertation values) and blood oxygen saturation level included in the biometric information, and generate a content of the guide message (i.e., a warning notification) on the dangerous situation. The processor 170 of the wearable device 10 may output a guide message, which may further include a user's exposure time to the harmful gas. In addition, the processor 170 of the wearable device 10 may control the communication circuitry 120 to transmit a sharing request, to share the guide message regarding the dangerous situation with some external device, to the server 30.

By monitoring the air quality information and the user biometric information together, the wearable device 10 may appropriately notify a user regarding a present dangerous situation that has arisen via changes in the external environment.

Figure 5:
FIG. 5 is a table illustrating a guide message according to biometric information and air quality information.

FIG. 5 is a table illustrating a guide message according to biometric information and air quality information. The information indicated in FIG. 5 may set pre-determined thresholds to trigger some or all of the operations indicated in this disclosure.

At least one of the wearable device 10, the electronic device 20, and the server 30 may store guide data related to the air quality information and the biometric information. The guide data may include prestored guide messages corresponding to the air quality and biometric information, for selection and output. In response to receiving the air quality information from the electronic device 20, and in response to obtaining the biometric information by the biosensor 130, the wearable device 10 may provide a guide message to the user with reference to the illustrated guide data. In some embodiments, the guide message may also be provided through the (external) electronic device 20.

The processor 170 of the wearable device 10 may determine the dangerous situation based on the air quality information and the biometric information, and may control the display 110 to output a guide message regarding the dangerous situation. Further, the processor 170 of the wearable device 10 may control a sound output device (e.g., a speaker) of the wearable device 10 to output the guide message (e.g., via vocal readback of the prestored guide message). The guide message may be output through the display 210 of the electronic device 20.

The wearable device 10 may provide information on the dangerous situation through an external electronic device (not shown) operatively connected to the electronic device 20 or the wearable device 10. For example, the wearable device 10 may provide information on the dangerous situation through an external electronic device connected through short-range communication (e.g., Wi-fi or Bluetooth) in an Internet of things (IoT) environment. The wearable device 10 may provide information on the dangerous situation through an external electronic device connected to the server 30 through the same account.

Referring to a table 500 of FIG. 5, a guide message provided based on a blood oxygen saturation level (SpO2), a concentration of carbon monoxide (CO), and a concentration of carbon dioxide (CO2) is exemplified. Carbon monoxide and carbon dioxide may be exemplified as representative gas that may threaten the health and safety of users in daily life. When at least one of the concentration of carbon monoxide and the concentration of carbon dioxide in the space where the user is located increases, the user's health and safety may be threatened. In addition to the examples, a guide message based on other biometric information such as a heart rate may be provided, and a guide message based on other types of harmful gas may be provided. Further, the numerical values illustrated in the table 500 of FIG. 5 may be changed or varied according to the user's situation, external environment, internal environment, and/or condition. In response to the blood oxygen saturation level being greater than or equal to 95, but less than or equal to 100, the user state may be determined as the normal state. In response to the blood oxygen saturation level being greater than or equal to 90, but less than 95, hypoxia may occur, and the user state may be determined as the caution state. In response to the blood oxygen saturation level being less than 90, breathing difficulties may occur due to hypoxia, and the user state may be determined as the dangerous state. When the user is exposed to the harmful gas, the blood oxygen saturation level may decrease. There may be various types of harmful gas that affect blood oxygen saturation level, but the harmful gas that has an immediate effect on changes in blood oxygen saturation level may be carbon monoxide (CO).

For example, when a user is exposed to a "very low" concentration (e.g., present value less than 50 ppm) of carbon monoxide (CO), the user's blood oxygen saturation level (SpO2) may be greater than 95, and the user state may be determined as the normal state. When the user is exposed to a low concentration (e.g., greater than or equal to 50 ppm, but less than 400 ppm) of carbon monoxide (CO), the user's blood oxygen saturation level (SpO2) may be greater than or equal to 91, but less than or equal to 95, and the user state may be determined as the caution state. In response to the blood oxygen saturation level (SpO2) being greater than or equal to 91, but less than or equal to 95, a guide message such as "hypoxia caution" may be provided.

In addition, when the user is exposed to a "high" concentration (e.g., present value greater than 400 ppm) of carbon monoxide (CO), the user's blood oxygen saturation level (SpO2) may be less than 90, and the user's state may be determined as the dangerous state. High concentrations of carbon monoxide (CO) may be due to fire. Therefore, in response to the blood oxygen saturation level being less than 90, a guide message such as "fire/suffocation warning" may be provided. Although not shown in the table 500, in response to the concentration of carbon monoxide (CO) being greater than or equal to 50 ppm, the guide message may include a content recommending ventilation.

In response to the blood oxygen saturation level being within a "normal" range, the content of the guide message may be determined based on the air quality. For example, the content of the guide message may be determined according to the concentration of carbon dioxide. In response to the user state determined by the blood oxygen saturation level being normal, the concentration of carbon monoxide (CO) being very low, and the concentration of carbon dioxide (CO2) being also very low (e.g., present value less than 2000 ppm), the content of the guide message "comfortable" may be provided. In response to the user state determined by the blood oxygen saturation level being normal, the concentration of carbon monoxide (CO) being very low, and the concentration of carbon dioxide (CO2) being also very low (e.g., less than 2000 ppm), the guide message may be omitted.

The physiological risk may increase as the user is exposed to the high concentration of carbon dioxide. In response to the concentration of carbon dioxide increasing even when the user condition is normal and the concentration of carbon monoxide is very low, ventilation may be utilized for user safety. For example, in response to the concentration of carbon dioxide (CO2) being greater than or equal to 2000 ppm, but less than or equal to 5000 ppm, a guide message recommending ventilation may be provided. In addition, in response to the concentration of carbon dioxide (CO2) exceeding 5000 ppm, a guide message strongly recommending ventilation may be provided.

On the other hand, when the user is not located in a location where the harmful gas is present, the user blood oxygen saturation level obtained by the wearable device 10 may be within the normal range, but the concentration of carbon monoxide (CO) obtained by the electronic device 20 may be high. In this case, the user may not be directly affected by the harmful gas, but the wearable device 10 may generate a notification that there is a risk in the location where the electronic device 20 is located.

As mentioned above, air quality management and/or user safety management may be induced by providing the guide message through at least one of the wearable device 10 and the electronic device 20.

Figure 6:
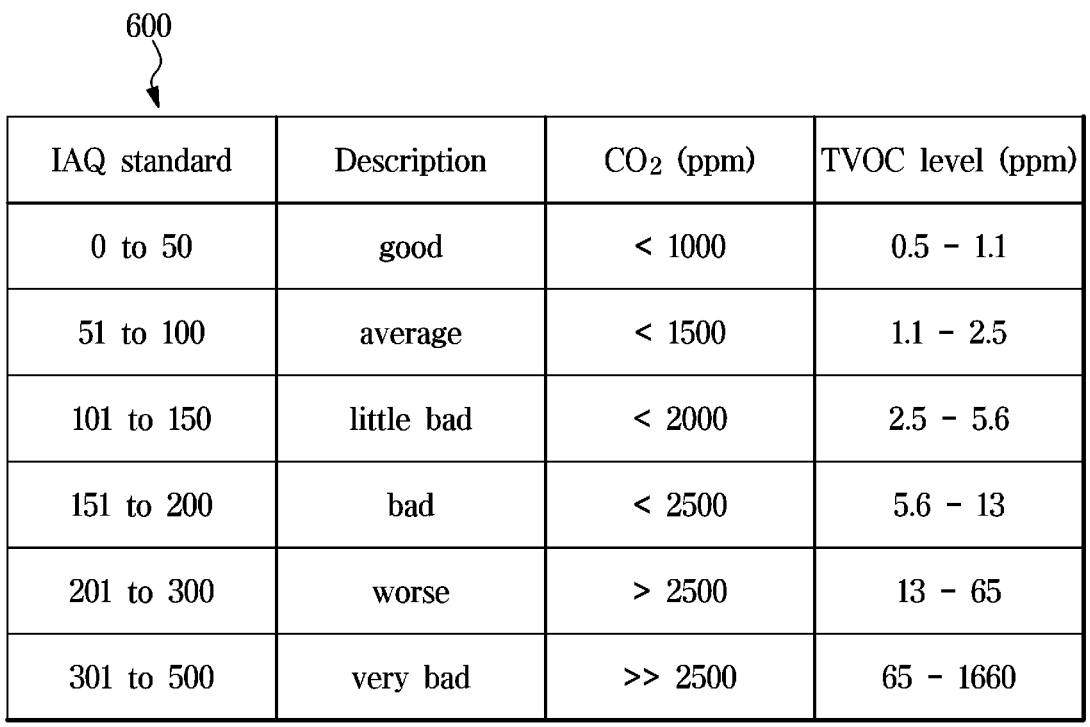
FIG. 6 is a table illustrating standards related to indoor air quality.

FIG. 6 is a table illustrating standards related to indoor air quality

Referring to a table 600 of FIG. 6, standards regarding indoor air quality (IAQ) are established based on the concentration of carbon dioxide (CO2) and the concentration of total volatile organic compounds (TVOC). The concentration of total volatile organic compounds (TVOC) may also correspond to an indicator to be monitored for the health and safety of users. A volatile organic compound means a liquid or gaseous organic compound that has a low boiling point and is easily evaporated into the atmosphere. The volatile organic compounds may cause photochemical smog by generating photochemical oxidizing agents such as ozone through a photochemical reaction with nitrogen oxides (NOx) in the atmosphere. In addition, substances such as benzene are carcinogenic and very harmful to the human body.

In response to the concentration of carbon dioxide (CO2) being less than 1000 ppm and the concentration of total volatile organic compounds (TVOC) being greater than or equal to 0.5 ppm, but less than 1.1 ppm, the indoor air quality (IAQ) index may be indicated as greater than or equal to 0 but less than or equal to 50, and the indoor air quality (IAQ) may be described as "good". In response to the concentration of carbon dioxide (CO2) being greater than or equal to 1000 ppm, but less than 1500 ppm, and the concentration of total volatile organic compounds (TVOC) being greater than or equal to 1.1 ppm, but less than 2.5 ppm, the indoor air quality (IAQ) index may be indicated as greater than or equal to 51 but less than or equal to 100, and the indoor air quality (IAQ) may be described as "average". In response to the concentration of carbon dioxide (CO2) being greater than or equal to 1500 ppm, but less than 2000 ppm, and the concentration of total volatile organic compounds (TVOC) being greater than or equal to 2.5 ppm, but less than 5.6 ppm, the indoor air quality (IAQ) index may be indicated as greater than or equal to 101 but less than or equal to 150, and the indoor air quality (IAQ) may be described as "little bad".

In response to the concentration of carbon dioxide (CO2) being greater than or equal to 2000 ppm, but less than 2500 ppm, and the concentration of total volatile organic compounds (TVOC) being greater than or equal to 5.6 ppm, but less than 13 ppm, the indoor air quality (IAQ) index may be indicated as greater than or equal to 151 but less than or equal to 200, and the indoor air quality (IAQ) may be described as "bad". In response to the concentration of carbon dioxide (CO2) being greater than or equal to 2500 ppm, and the concentration of total volatile organic compounds (TVOC) being greater than or equal to 13 ppm, but less than 65 ppm, the indoor air quality (IAQ) index may be indicated as greater than or equal to 201 but less than or equal to 300, and the indoor air quality (IAQ) may be described as "worse". In response to the concentration of carbon dioxide (CO2) being further greater than 2500 ppm, and the concentration of total volatile organic compounds (TVOC) being greater than or equal to 65 ppm, but less than 1660 ppm, the indoor air quality (IAQ) index may be indicated as greater than or equal to 301 but less than or equal to 500, and the indoor air quality (IAQ) may be described as "very bad".

Figure 7:
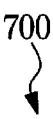
FIG. 7 is a table illustrating guides according to an exposure time to harmful gas.

FIG. 7 is a table illustrating guides according to an exposure time to harmful gas.

As described above, at least one of the wearable device 10 or the electronic device 20 may display the guide message determined based on the air quality information and the user biometric information. In addition, at least one of the wearable device 10 or the electronic device 20 may determine the content of the guide message by further considering the user's exposure time to the harmful gas. In a table 700 of FIG. 7, a guide is illustrated indicating relationships between the concentration and exposure time of carbon monoxide (CO) in the harmful gas and the time to display a warning.

For example, when the concentration of carbon monoxide (CO) is less than 50 ppm, the user health is not affected, and thus the warning may not be provided. However, in the following cases, a guide message warning that the user safety is threatened may be provided:
  i) When the user is continuously exposed to carbon monoxide (CO) having the concentration of greater than or equal to 50 ppm but less than 70 ppm for 30 days or more,
  ii) When the user is continuously exposed to carbon monoxide (CO) having the concentration of greater than or equal to 70 ppm but less than or equal to 149 ppm for 60 minutes or more,
  iii) When the user is continuously exposed to carbon monoxide (CO) having the concentration of greater than or equal to 150 ppm but less than or equal to 399 ppm for 10 minutes or more, and
  iv) When the user is continuously exposed to carbon monoxide (CO) having the concentration of greater than or equal to 400 ppm for more than 4 minutes.

As mentioned above, by providing the guide message based at least in part on the user exposure time to the harmful gas, it is possible to prevent accidents and to notify the user to take appropriate safety measures in dangerous or potentially dangerous situations.

Figure 8:
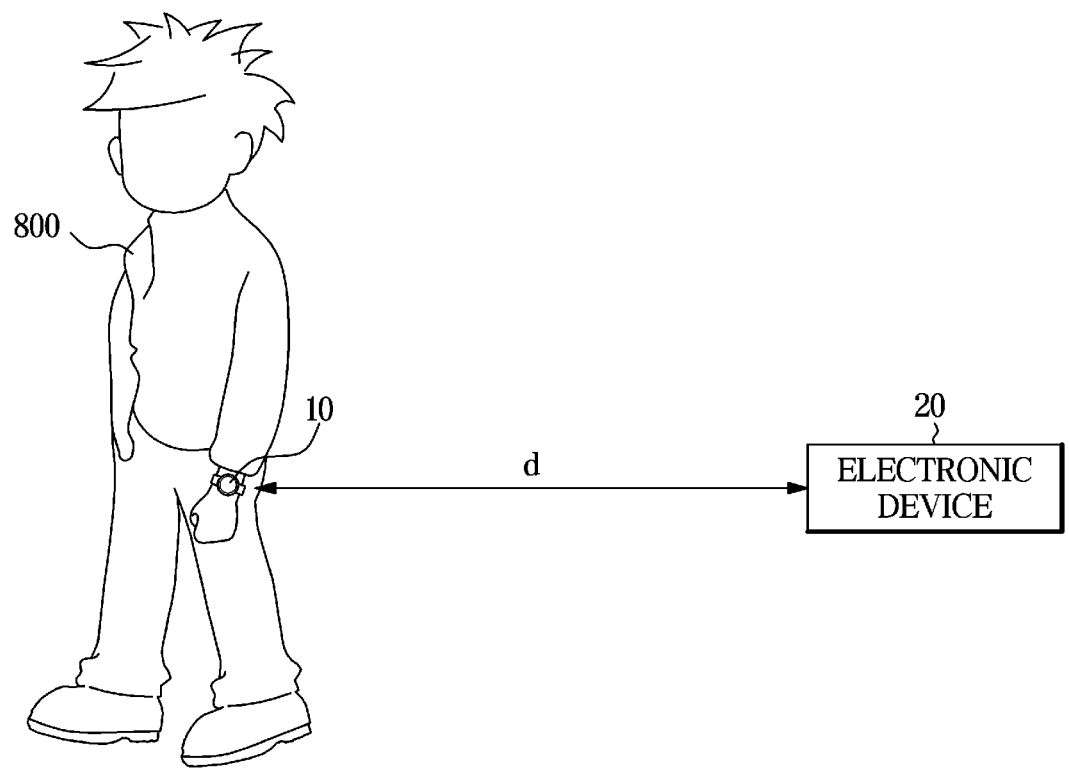
FIG. 8 illustrates estimation of a concentration of harmful gas in consideration of a distance between the wearable device and the electronic device.

FIG. 8 illustrates estimation of a concentration of harmful gas in consideration of a distance between the wearable device and the electronic device.

Referring to FIG. 8, the processor 170 of the wearable device 10 may determine a distance d from the external electronic device 20 based on at least one of distance data obtained by the distance sensor 140 or a signal strength of the electronic device 20. The processor 170 of the wearable device 10 may estimate the concentration of the harmful gas at the user' location 800 based on the distance d from the electronic device 20. The processor 170 of the wearable device 10 may determine a dangerous situation based on the estimated concentration of harmful gas and the blood oxygen saturation level, and may determine the content of the guide message regarding the dangerous situation.

As the distance between the wearable device 10 and the electronic device 20 is increased, the signal strength of the electronic device 20 received by the wearable device 10 is decreased. Therefore, the distance may be further or alternatively calculated using the signal strength of the electronic device 20. The distance measurement method may be a received signal strength indicator (RSSI) method.

A Time of Arrival (TOA) method may be used as another method of measuring the distance. The TOA method may calculate the distance by using a time delay value of signals sent and received between the transmitter and the receiver.

Further, each of the wearable device 10 and the electronic device 20 may further include a GPS receiver configured to obtain location information. The processor 170 of the wearable device 10 may determine the distance d to the electronic device 20 based on the location information of the wearable device 10 and the location information of the electronic device 20. The distance between the wearable device 10 and the electronic device 20 may be measured by the electronic device 20.

The distance and/or direction between the wearable device 10 and the electronic device 20 may be calculated using a time difference between a transmission signal generated by the wearable device 10 and a reflection signal returned from the electronic device 20. When the wearable device 10 and the electronic device 20 are connected by an ultra-wideband (UWB) communication technology, an accuracy of distance measurement may be improved relative to other communication methods.

When the user wearing the wearable device 10 is located outside a predetermined distance from the external electronic device 20 that obtains air quality information, air quality information obtained by the electronic device 20 may be different from air quality of a place where the user is actually located. For example, the user wearing the wearable device 10 in a house may be located in a living room, and the electronic device 20 including the gas sensor 230 may be located in another room different from the living room. When harmful gas is generated in the other room, the concentration of the harmful gas measured in the other room may be different from the concentration of the harmful gas around the user located in the living room. The harmful gas generated in the other room may spread over time and reach the user's location.

The processor 170 of the wearable device 10 may estimate a concentration of harmful gas in the user's location by using the distance between the wearable device 10 and the electronic device 20, a diffusion rate of the harmful gas, and the concentration of the harmful gas obtained by the electronic device 20. The diffusion rate and diffusion coefficient according to the type of harmful gas may be pre-stored in at least one of the wearable device 10, the electronic device 20, and the server 30.

As mentioned above, by linking the concentration of the harmful gas estimated at the user's actual location to the biometric information, it is possible to more accurately provide the user with the guide to the dangerous situation.

Meanwhile, when the electronic device 20 is within the distance in which the short-range communication with the wearable device 10 is available, the processor 170 of the wearable device 10 may determine that the user is directly affected by air quality. Therefore, in response to the connection between the wearable device 10 and the electronic device 20 by the short-distance communication, a guide message requesting an active measure may be provided.

Figure 9:
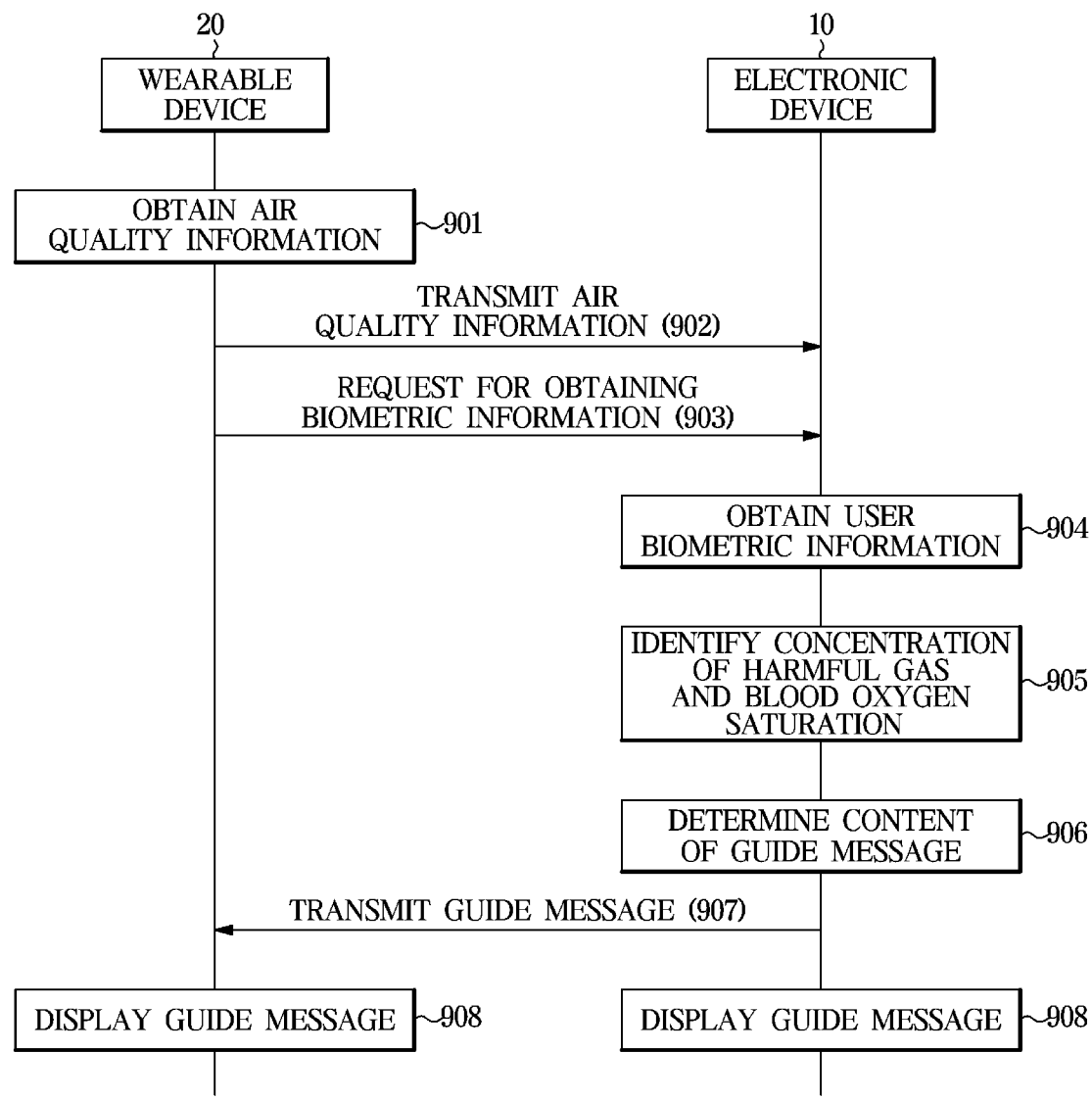
FIG. 9 is a flowchart illustrating operations of the wearable device and the electronic device according to an embodiment of the present disclosure.

FIG. 9 is a flowchart illustrating operations of the wearable device and the electronic device according to an embodiment of the present disclosure.

Referring to FIG. 9, the electronic device 20 may obtain air quality information (901). The electronic device 20 may obtain air quality information at a predetermined interval or intervals. Further, the electronic device 20 may receive a request for obtaining air quality information from the wearable device 10 or the server 30, and may obtain the air quality information in response to the request. For example, in response to fire event information being transmitted from another electronic device 21, the server 30 may request the electronic device 20 to obtain the air quality information.

The air quality information may include concentration data of harmful gas, and may further include temperature data and humidity data. The electronic device 20 may transmit the obtained air quality information to the wearable device 10 (902). The electronic device 20 may request the wearable device 10 to obtain biometric information (903). For example, in response to the concentration of the harmful gas contained in the air quality information exceeding a predetermined threshold value, the electronic device 20 may request the wearable device 10 to obtain the biometric information.

The wearable device 10 may control the biosensor 130 to obtain the biometric information in response to the request for obtaining biometric information received from the electronic device 20 (904). Alternatively, the wearable device 10 may periodically obtain the biometric information, or obtain biometric information upon reception of a user input.

The wearable device 10 may identify the concentration of harmful gas in the air quality information and identify the blood oxygen saturation level in the biometric information (905). The wearable device 10 may determine a dangerous situation based on the concentration of harmful gas and the blood oxygen saturation level, and may determine the content of the guide message regarding the dangerous situation (906). The wearable device 10 may provide a guide message by applying further the user's exposure time to the harmful gas.

The wearable device 10 may transmit the guide message to the electronic device 20 (907) and display the guide message on the display 110 (908). The electronic device 20 may display the guide message received from the wearable device 10 on the display 210 (908).

The determination of the dangerous situation based on the air quality information and the biometric information may be performed by the electronic device 20. That is, the electronic device 20 may determine the dangerous situation based on the obtained air quality information and the biometric information transmitted from the wearable device 10.

As mentioned above, by monitoring the air quality information together with the user biometric information and by providing a notification according to the monitoring result, it is possible to secure the health and safety of the user.

Figure 10:
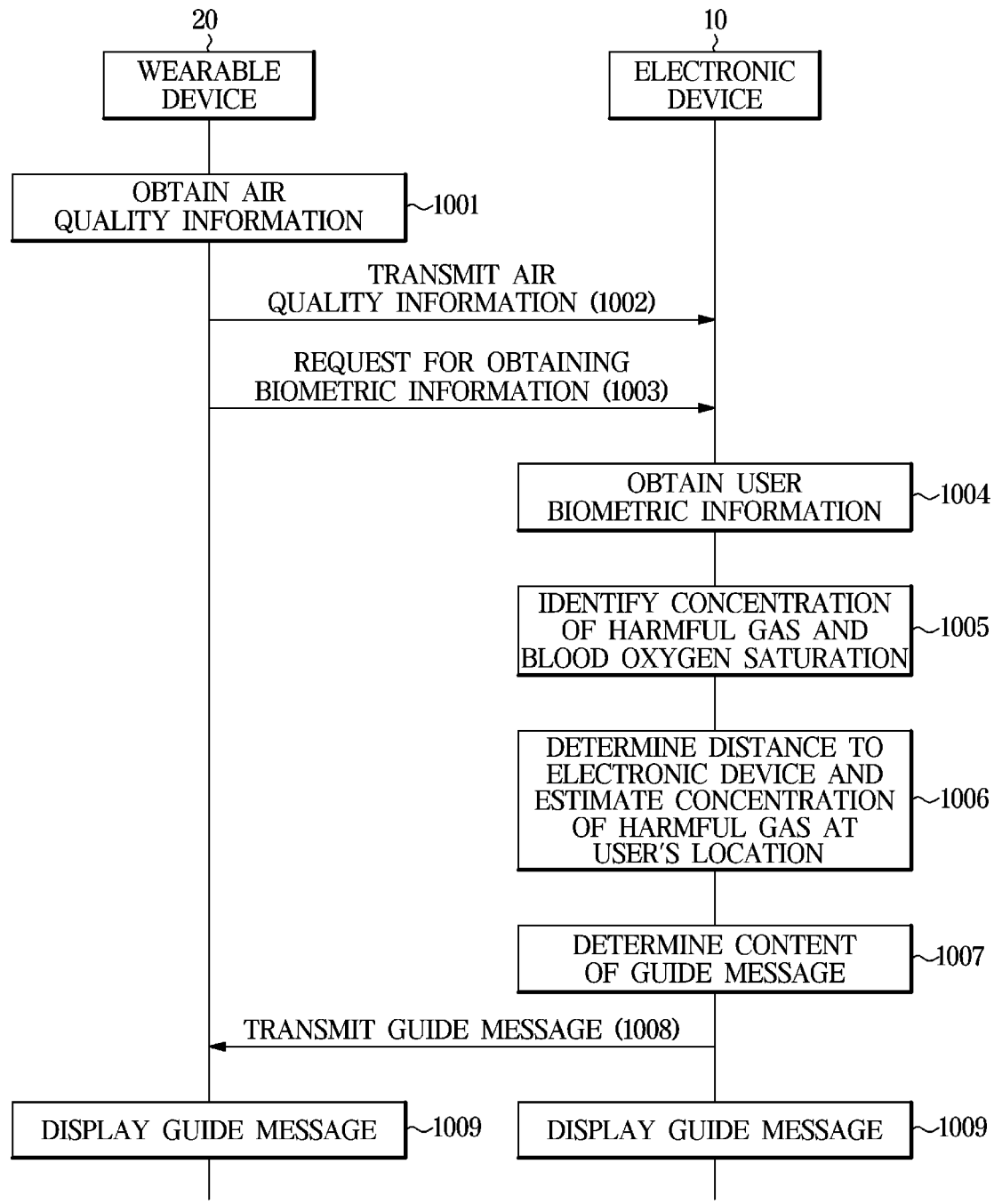
FIG. 10 is a flowchart illustrating in more detail operations of the wearable device and the electronic device according to an embodiment of the present disclosure.

FIG. 10 is a flowchart illustrating in more detail operations of the wearable device and the electronic device according to an embodiment of the present disclosure.

Referring to FIG. 10, the electronic device 20 may obtain air quality information (1001). The air quality information may include concentration data of harmful gas, and may further include temperature data and humidity data. The electronic device 20 may transmit the obtained air quality information to the wearable device 10 (1002). The electronic device 20 may request the wearable device 10 to obtain biometric information (1003). The wearable device 10 may control the biosensor 130 to obtain the biometric information in response to the request for obtaining the biometric information received from the electronic device 20 (1004). Alternatively, the wearable device 10 may periodically obtain the biometric information or obtain biometric information based on a user input.

The wearable device 10 may identify the concentration of harmful gas in the air quality information and identify the blood oxygen saturation level in the biometric information (1005). Further, the wearable device 10 may determine the distance to the electronic device 20 and estimate the concentration of the harmful gas at the user's location based on the distance to the electronic device 20 (1006). The wearable device 10 may determine the distance to the electronic device 20 based on at least one of distance data obtained by the distance sensor 140 or a signal strength of the electronic device 20. The wearable device 10 may determine a dangerous situation based on the estimated concentration of harmful gas and blood oxygen saturation level, and may determine the content of a guide message regarding the dangerous situation (1007). The wearable device 10 may provide a guide message based further in consideration of the user's exposure time to the harmful gas, as described above.

The wearable device 10 may transmit the guide message to the electronic device 20 (1008), and may display the guide message on the display 110 (1009). The electronic device 20 may also display the guide message received from the wearable device 10 on the display 210 (1009).

As mentioned above, by linking the concentration of the harmful gas that is estimated at the user's actual location to the biometric information, it is possible to more accurately provide the user with the guide to the dangerous situation.

Figure 11:
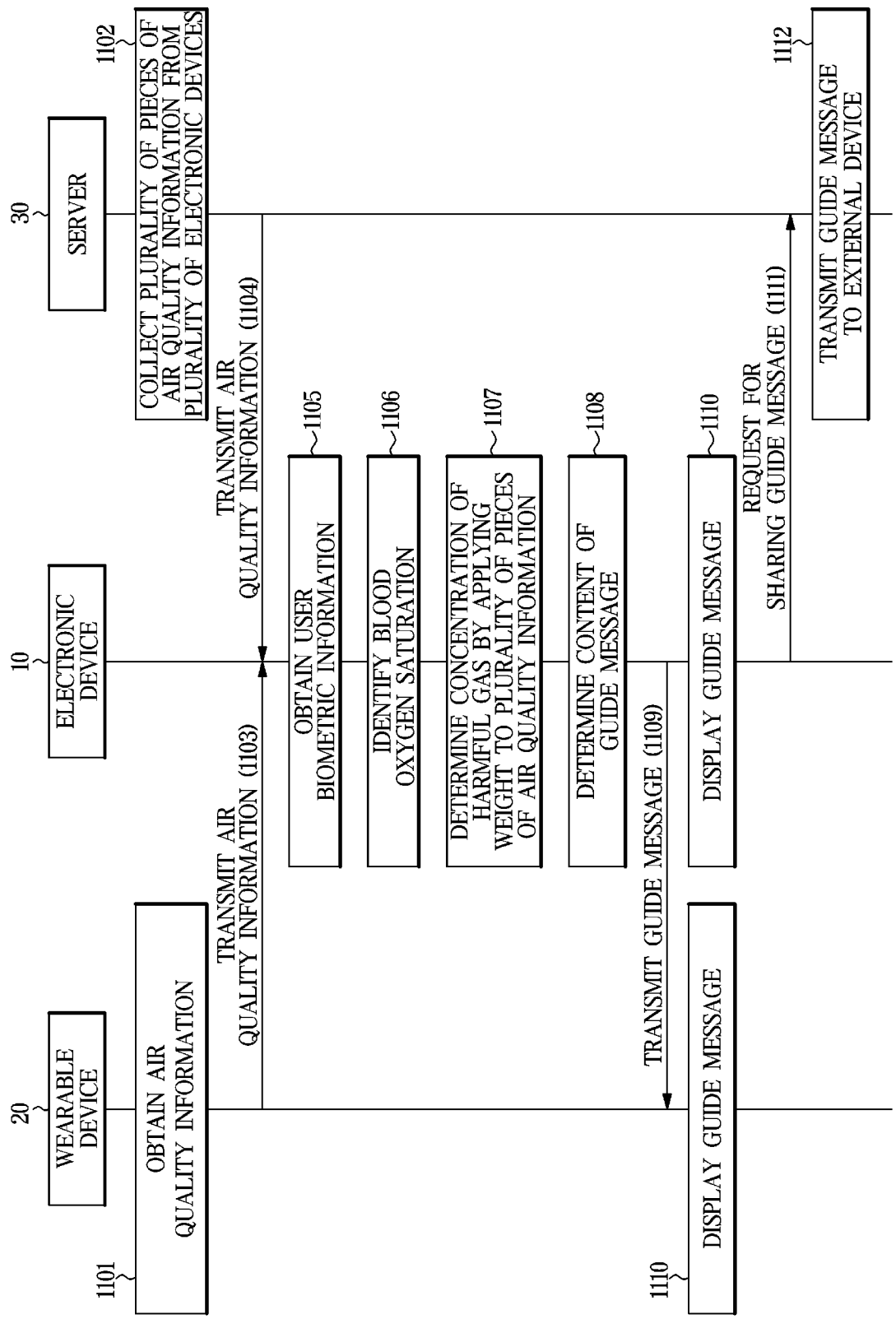
FIG. 11 is a flowchart illustrating operations of the wearable device, the electronic device, and a server according to an embodiment of the present disclosure.

FIG. 11 is a flowchart illustrating operations of the wearable device, the electronic device, and a server according to an embodiment of the present disclosure.

Referring to FIG. 11, the electronic device 20 may obtain air quality information (1101) and transmit the air quality information to the wearable device 10 (1103). Meanwhile, when a plurality of electronic devices 20 and 21 is provided, air quality information obtained by the plurality of electronic devices 20 and 21 may be transmitted to the server 30. The server 30 may collect air quality information transmitted from the plurality of electronic devices 20 and 21 (1102), and transmit the collected air quality information to the wearable device 10 (1104).

The wearable device 10 may obtain biometric information (1105). The wearable device 10 may periodically obtain the biometric information, or obtain biometric information upon reception of a user input, or obtain biometric information in response to a request for obtaining biometric information received from the electronic device 20 or the server 30. The wearable device 10 may identify the blood oxygen saturation level from the biometric information (1106).

The wearable device 10 may determine the concentration of harmful gas by applying a respective weight to each of the plurality of pieces of air quality information (1107). The wearable device 10 may receive information on the concentration of harmful gas determined using the plurality of pieces of air quality information from the electronic device 20 or the server 30. The weight may be determined based on a sensitivity constant for each of the plurality of electronic devices 20 and 21 that obtains air quality information.

The gas sensor 230 included in each of the plurality of electronic devices 20 and 21 may have a predetermined sensitivity constant. The sensitivity constant is an index indicating the performance of the gas sensor 230 and may indicate selectivity for a specific gas. A weight may also be referred to as a sensitivity fraction. The weight corresponds to a value obtained by dividing the sensitivity constant of each gas sensor 230 by the sum of all sensitivity constants. The weight may be determined by an equation 1 below.

Weight of gas sensor $(a\_n)$=sensitivity constant of gas sensor $(b\_n)$/sum of sensitivity constants of a plurality of gas sensors $(\Sigma b\_n)$     [Equation 1]

A final concentration of the harmful gas may be determined as the sum of the values obtained by multiplying the concentration of the harmful gas, which is obtained by the respective electronic devices 20 and 21, by the weights of the respective electronic devices 20 and 21. That is, the final concentration of harmful gas may be determined by an equation 2 below.

Concentration of harmful gas [$C\_final$]=first weight ($a\_1$)*first concentration ($C1$)+second weight ($a\_2$)*second concentration ($C2$)  [Equation 2]

To describe the equation 2, the final concentration ($C\_final$) of the harmful gas is obtained by summing a value, which is obtained by multiplying the first weight $a\_1$ by the first concentration $C1$ of the harmful gas obtained by the first electronic device 20, and a value, which is obtained by multiplying the second weight $a\_2$ by the second concentration $C2$ of the harmful gas obtained by the second electronic device 21. Accordingly, by using the plurality of pieces of air quality information, the accuracy regarding the concentration of the harmful gas may be improved.

The wearable device 10 may determine the dangerous situation based on the concentration of harmful gas and blood oxygen saturation level, and may determine the content of the guide message regarding the dangerous situation (1108). The wearable device 10 may provide a guide message based further on the user's exposure time to the harmful gas. The wearable device 10 may transmit the guide message to the electronic device 20 (1109) and display the guide message on the display 110 (1110). The electronic device 20 may also display the guide message received from the wearable device 10 on the display 210 (1110).

Further, the processor 170 of the wearable device 10 may control the communication circuitry 120 to transmit a sharing request to share the guide message regarding the dangerous situation with an external device, to the server 30 (1111). The server 30 may transmit the guide message to the external device (1112). The external device may output the received guide message. For example, the external device may include a device linked to the user account, a device belonging to an acquaintance, or a device belonging to a family member stored in contact information. Further, the external device may belong to a rescue organization, which may more rapidly dispatch an official response to the dangerous situation. As mentioned above, by sharing the guide message regarding the dangerous situation with the external device, it is possible to more efficiently perform measures for user safety.

The determination of the dangerous situation, the provision of the guide message related to the dangerous situation, and the request for sharing the guide message may be performed by the electronic device 20. That is, the processor 270 of the electronic device 20 may determine the dangerous situation based on the air quality information and the biometric information transmitted from the wearable device 10, and control the display 210 to provide the guide message regarding the dangerous situation according to the determination result.

As described above, the disclosed wearable device, the system including the wearable device and the electronic device, and the method may provide the guide to the health and safety of the user by linking the air quality information obtained by a separate electronic device to the user biometric information.

The disclosed wearable device, the system including the wearable device and the electronic device, and the method may monitor the air quality information of the location where the electronic device is located and the user biometric information together, so as to notify the user of a possible dangerous situation caused by a change in the external environment.

Figure 12:
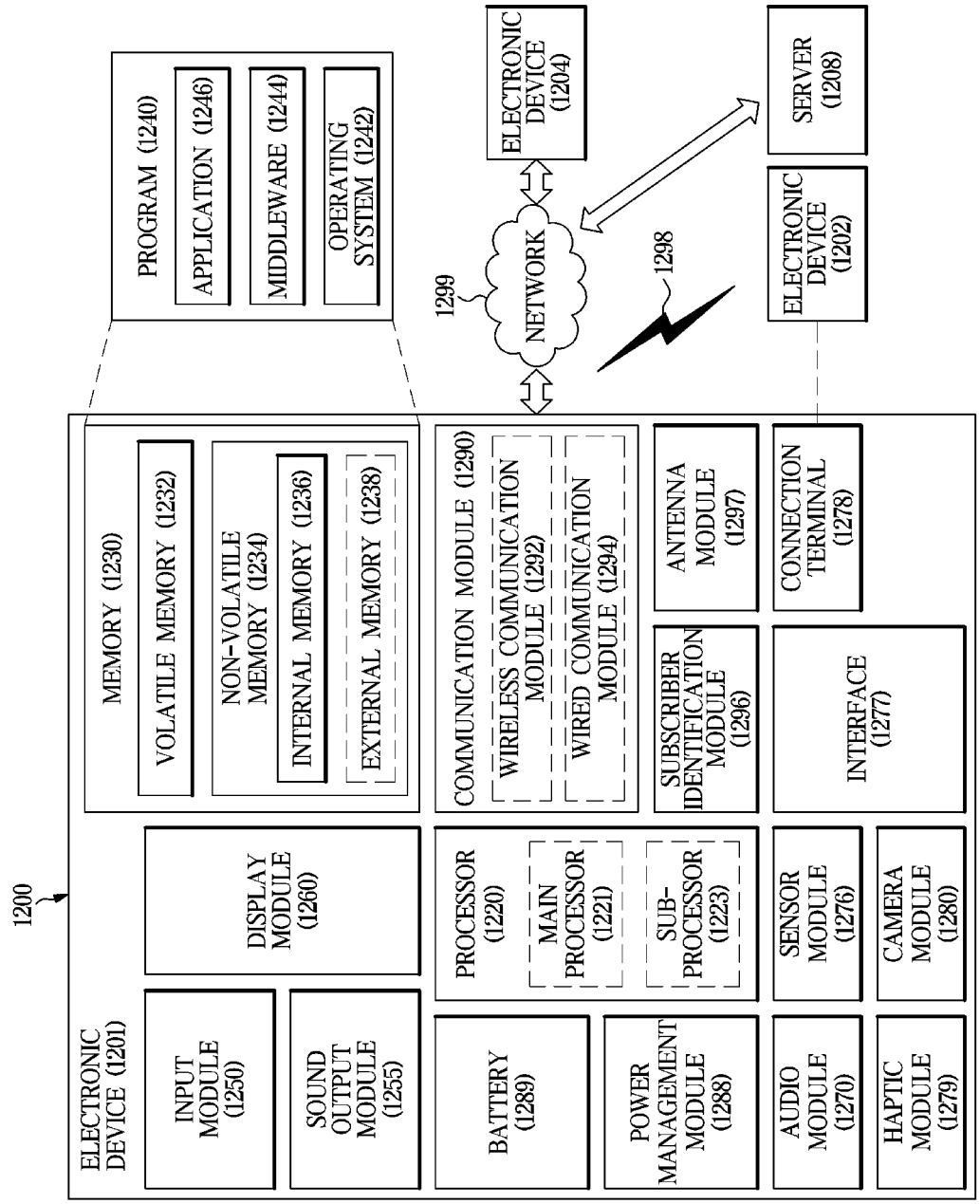
FIG. 12 is a block diagram of an electronic device in a network environment 1200 according to certain embodiments of the present disclosure.

FIG. 12 is a block diagram of an electronic device 1201 in a network environment 1200 according to certain embodiments of the present disclosure.

Referring to FIG. 12, in the network environment 1200, the electronic device 1201 may communicate with at least one of an electronic device 1202 through a first network 1298 (e.g., a short-range wireless communication network) or an electronic device 1204 and a server 1208 through a second network 1299 (e.g., a long-distance wireless communication network). According to an embodiment, the electronic device 1201 may communicate with the electronic device 1204 through the server 1208. According to an embodiment, the electronic device 1201 may include a processor 1220, a memory 1230, an input module 1250, a sound output module 1255, a display module 1260, an audio module 1270, and a sensor module 1276, an interface 1277, a connection terminal 1278, a haptic module 1279, a camera module 1280, a power management module 1288, a battery 1289, a communication module 1290, a subscriber identification module 1296, or an antenna module 1297. According to some embodiments, at least one of these components (e.g., the connection terminal 1278) may be omitted or one or more other components may be added to the electronic device 1201. According to some embodiments, some of these components (e.g., the sensor module 1276, the camera module 1280, or the antenna module 1297) may be integrated into one component (e.g., the display module 1260).

The processor 1220 may execute software (e.g., a program 1240) to control at least one other component (e.g., a hardware or software component) of the electronic device 1201 connected to the processor 1220, and perform various data processing or operations. According to an embodiment, as at least part of data processing or operation, the processor 1220 may store instructions or data received from other components (e.g., the sensor module 1276 or the communication module 1290) in the volatile memory 1232, process the instructions or data stored in the volatile memory 1232, and store the result data in the non-volatile memory 1234. According to an embodiment, the processor 1220 may include a main processor 1221 (e.g., a central processing unit or an application processor) or a sub-processor 1223 (e.g., a graphics processing unit, a neural network processing unit (NPU), an image signal processor, a sensor hub processor, or a communication processor) that is operated independently of the main processor or operated together with the main processor. For example, when the electronic device 1201 includes the main processor 1221 and the sub-processor 1223, the sub-processor 1223 may use less power than the main processor 1221 or set to be specialized for a specified function. The sub-processor 1223 may be implemented separately from the main processor 1221 or implemented as part of the main processor 1221.

On behalf of the main processor 1221 when the main processor 1221 is in an inactive (e.g., sleep) state, or together with the main processor 1221 when the main processor 1221 is in an active (e.g., execution of an application) state, the sub-processor 1223 may control at least one of functions or states related to at least one component (e.g., the display module 1260, the sensor module 1276, or the communication module 1290) among components of the electronic device 1201. According to an embodiment, the sub-processor 1223 (e.g., an image signal processor or a communication processor) may be implemented as a part of another functionally related component (e.g., the camera module 1280 or the communication module 1290). According to an embodiment, the sub-processor 1223 (e.g., the neural network processing unit) may include a hardware structure specialized for processing an artificial intelligence model. The artificial intelligence models may be generated through machine learning. The learning may be performed in the electronic device 1201 itself in which the artificial intelligence model is performed, or may be performed through a separate server (e.g., the server 1208). A learning algorithm may include supervised learning, unsupervised learning, semi-supervised learning, or reinforcement learning, but is not limited to thereto. The artificial intelligence model may include a plurality of artificial neural network layers. Artificial neural networks may be deep neural networks (DNNs), convolutional neural networks (CNNs), recurrent neural networks (RNNs), restricted Boltzmann machines (RBMs), deep belief networks (DBNs), bidirectional recurrent deep neural networks (BRDNNs), deep Q-networks or a combination of two or more of these networks, but is not limited to thereto. The artificial intelligence model may additionally or alternatively include a software structure in addition to the hardware structure.

The memory 1230 may store various data used by at least one component (e.g., the processor 1220 or the sensor module 1276) of the electronic device 1201. The data may include software (e.g., the program 1240) and input data or output data for and instructions related to the software. The memory 1230 may include a volatile memory 1232 or a non-volatile memory 1234.

The program 1240 may be stored as software in the memory 1230, and may include an operating system 1242, a middleware 1244, or an application 1246.

The input module 1250 may receive instructions or data to be used by a component (e.g., the processor 1220) of the electronic device 1201 from the outside (e.g., a user) of the electronic device 1201. The input module 1250 may include a microphone, a mouse, a keyboard, a key (e.g., a button), or a digital pen (e.g., a stylus pen).

The sound output module 1255 may output a sound signal to the outside of the electronic device 1201. The sound output module 1255 may include a speaker or a receiver. The speaker may be used for general purposes such as multimedia playback or recording playback. The receiver may be used to receive incoming calls. According to an embodiment, the receiver may be implemented separately from the speaker or as part of the speaker.

The display module 1260 may visually provide information to the outside (e.g., a user) of the electronic device 1201. The display module 1260 may include a display, a hologram device, or a projector and a control circuit for controlling the corresponding device. According to an embodiment, the display module 1260 may include a touch sensor configured to sense a touch or a pressure sensor configured to measure an intensity of a force generated by the touch.

The audio module 1270 may convert a sound into an electric signal or, conversely, convert an electric signal into a sound. According to an embodiment, the audio module 1270 may obtain a sound through the input module 1250 or output a sound through an external electronic device (the electronic device 1202: e.g., a speaker or a headphone) directly or wirelessly connected to the electronic device 1201.

The sensor module 1276 may detect an operating state (e.g., power or temperature) of the electronic device 1201 or an external environmental state (e.g., user state), and generate an electrical signal or data value corresponding to the detected state. According to an embodiment, the sensor module 1276 may include a gesture sensor, a gyro sensor, an air pressure sensor, a magnetic sensor, an acceleration sensor, a grip sensor, a proximity sensor, a color sensor, an infrared (IR) sensor, a biosensor, a temperature sensor, a humidity sensor, or an illuminance sensor.

The interface 1277 may support one or more specified protocols that may be used for the electronic device 1201 to be directly or wirelessly connected to an external electronic device (e.g., the electronic device 1202). According to an embodiment, the interface 1277 may include a high-definition multimedia interface (HDMI), a universal serial bus (USB) interface, an SD card interface, or an audio interface.

The connection terminal 1278 may include a connector through which the electronic device 1201 may be physically connected to an external electronic device (e.g., the electronic device 1202). According to an embodiment, the connection terminal 1278 may include an HDMI connector, a USB connector, a SD card connector, or an audio connector (e.g., a headphone connector).

The haptic module 1279 may convert an electrical signal into a mechanical stimulus (e.g., vibration or movement) or an electrical stimulus that the user can perceive through tactile or kinesthetic sense. According to an embodiment, the haptic module 1279 may include a motor, a piezoelectric element, or an electrical stimulation device.

The camera module 1280 may image still images and moving images. According to an embodiment, the camera module 1280 may include one or more lenses, image sensors, image signal processors, or flashes.

The power management module 1288 may manage power supplied to the electronic device 1201. According to an embodiment, the power management module 1288 may be implemented as at least a part of a power management integrated circuit (PMIC).

The battery 1289 may supply power to at least one component of the electronic device 1201. According to an embodiment, the battery 1289 may include a non-rechargeable primary cell, a rechargeable secondary cell, or a fuel cell.

The communication module 1290 may establish a direct (e.g., wired) communication channel or a wireless communication channel between the electronic device 1201 and an external electronic device (e.g., the electronic device 1202, the electronic device 1204, or the server 1208) and support communication performance through the established communication channel. The communication module 1290 may include one or more communication processors configured to be operated independently of the processor 1220 (e.g., an application processor), and configured to support direct (e.g., wired) communication or wireless communication. According to an embodiment, the communication module 1290 may include a wireless communication module 1292 (e.g., a cellular communication module, a short-range wireless communication module, or a global navigation satellite system (GNSS) communication module) or a wired communication module 1294 (e.g., a local area network (LAN) communication module, or a power line communication module). A corresponding communication module among these communication modules may communicate with the external electronic device 1204 through a first network 1298 (e.g., a short-range communication network such as Bluetooth, wireless fidelity (Wi-Fi) direct, or infrared data association (IrDA)) or a second network 1299 (e.g., a long-distance communication network such as a legacy cellular network, a 5G network, a next-generation communication network, the Internet, or a computer network (e.g., LAN or WAN)). These various types of communication modules may be integrated into one component (e.g., a single chip) or may be implemented as a plurality of components (e.g., multiple chips) separate from each other. The wireless communication module 1292 may identify or authenticate the electronic device 1201 within a communication network, such as the first network 1298 or the second network 1299, by using subscriber information (e.g., International Mobile Subscriber Identifier (IMSI)) stored in the subscriber identification module 1296.

The wireless communication module 1292 may support a 5G network after a 4G network and a next-generation communication technology, for example, a new radio (NR) access technology. NR access technology may support enhanced mobile broadband (eMBB) that is high-speed transmission of high-capacity data, massive machine type communications (mMTC) that is minimization of terminal power and access to multiple terminals, or ultra-reliable and low-latency communications (URLLC). The wireless communication module 1292 may support a high frequency band (e.g., mmWave band) to achieve a high data transmission rate. The wireless communication module 1292 may support various techniques, such as beamforming, massive multiple-input and multiple-output (MIMO), full dimensional MIMO (FD-MIMO), an array antenna, analog beam-forming, or a large-scale antenna, for securing performance in a high-frequency band. The wireless communication module 1292 may support various operations of the electronic device 1201, an external electronic device (e.g., the electronic device 1204), or a network system (e.g., the second network 1299). According to an embodiment, the wireless communication module 1292 may support a peak data rate (e.g., 20 Gbps or more) for realization of eMBB, loss coverage for realization of mMTC (e.g., 164 dB or less), or U-plane latency (e.g., downlink (DL) and uplink (UL) of each 0.5 ms or less, or round trip of 1 ms or less) for realization of URLLC.

The antenna module 1297 may transmit or receive a signal or power to or from the outside (e.g., an external electronic device). According to an embodiment, the antenna module 1297 may include an antenna including a conductor formed on a substrate (e.g., a PCB) or a radiator formed of a conductive pattern. According to an embodiment, the antenna module 1297 may include a plurality of antennas (e.g., an array antenna). In this case, at least one antenna suitable for a communication method used in a communication network such as the first network 1298 or the second network 1299 may be selected from among the plurality of antennas by the communication module 1290. A signal or power may be transmitted or received between the communication module 1290 and an external electronic device through the selected at least one antenna. According to some embodiments, other components (e.g., a radio frequency integrated circuit (RFIC)) other than the radiator may be additionally formed as a part of the antenna module 1297.

According to certain embodiments, the antenna module 1297 may form a mmWave antenna module. According to an embodiment, the mmWave antenna module may include a printed circuit board, an RFIC arranged on or adjacent to a first surface (e.g., lower surface) of the printed circuit board and configured to support a designated high frequency band (e.g., mmWave band), and a plurality of antennas (e.g., an array antenna) arranged on or adjacent to a second surface (e.g., upper surface or lateral surface) of the printed circuit board and configured to transmit or receive signals of the designated high frequency band.

At least some of the components may be connected to each other through a communication method between peripheral devices (e.g., a bus, general purpose input and output (GPIO), serial peripheral interface (SPI), or mobile industry processor interface (MIPI)), and may exchange a signal (e.g., instructions or data) with each other.

According to an embodiment, the instruction or data may be transmitted or received between the electronic device 1201 and the external electronic device 1204 through the server 1208 connected to the second network 1299. Each of the external electronic devices 1202 or 1204 may be the same or a different type of the electronic device 1201. According to an embodiment, all or a part of the operations executed in the electronic device 1201 may be executed in one or more of the external electronic devices 1202, 1204, or 1208. For example, when the electronic device 1201 needs to perform a function or service automatically or in response to a request from a user or other device, the electronic device 1201 may perform the function or service by itself or additionally, may request one or more external electronic devices to perform at least a part of the function or the service. The one or more external electronic devices receiving the request may execute at least a part of the requested function or service, or an additional function or service related to the request, and transmit a result of the execution to the electronic device 1201. The electronic device 1201 may provide the result as at least a part of a response to the request, or additionally process the result and provide the processed result as at least a part of a response to the request. For this purpose, a technology such as cloud computing, distributed computing, mobile edge computing (MEC), or client-server computing may be used. The electronic device 1201 may provide an ultra-low latency service using distributed computing or mobile edge computing. In another embodiment, the external electronic device 1204 may include an Internet of things (IoT) device. The server 1208 may be an intelligent server using machine learning and/or neural networks. According to an embodiment, the external electronic device 1204 or the server 1208 may be included in the second network 1299. The electronic device 1201 may be applied to an intelligent service (e.g., smart home, smart city, smart car, or health care) based on 5G communication technology and IoT-related technology.

The electronic device according to certain embodiments disclosed in the present disclosure may have various types of devices. For example, the electronic device may include a portable communication device (e.g., a smart phone), a computer device, a portable multimedia device, a portable medical device, a camera, a wearable device, or a home appliance device. The electronic device according to the embodiment of the present disclosure is not limited to the above-described devices.

The certain embodiments and the terms used therein are not intended to limit the technology disclosed herein to specific forms, and the present disclosure should be understood to include various modifications, equivalents, and/or alternatives to the corresponding embodiments. In describing the drawings, similar reference numerals may be used to designate similar constituent elements. A singular expression may include a plural expression unless they are definitely different in a context. The expressions "A or B," "at least one of A or/and B," or "one or more of A or/and B," and the like used herein may include any and all combinations of one or more of the associated listed items. Herein, the expressions "a first", "a second", "the first", "the second", etc., may simply be used to distinguish an element from other elements, but is not limited to another aspect (importance or order) of elements. When an element (e.g., a first element) is referred to as being "(functionally or communicatively) coupled," or "connected" to another element (e.g., a second element), the first element may be connected to the second element, directly (e.g., wired), wirelessly, or through a third component.

As used herein, the term "module" may refer to a unit that includes one or a combination of two or more of hardware, software, or firmware. A "module" may be interchangeably used with terms such as, for example, unit, logic, logical block, component, or circuit. The module may be a minimum unit or part of an integrally implemented part. The module may be a minimum unit or part of performing one or more functions. The "module" can be implemented mechanically or electronically. For example, a "module" may be implemented in the form of an application-specific integrated circuit (ASIC).

Certain embodiments of the present document may be implemented as software (e.g., the program 1240) including one or more instructions stored in a storage medium (e.g., an internal memory 1236 or an external memory 1238) readable by a machine (e.g., the electronic device 1201). For example, a processor (e.g., the processor 1220) of a device (e.g., the electronic device 1201) may call at least one instruction among one or more instructions stored in a storage medium and execute the instruction. This makes it possible for the device to be operated to perform at least one function according to the called at least one instruction. The one or more instructions may include code generated by a compiler or code executable by an interpreter. Storage medium readable by machine, may be provided in the form of a non-transitory storage medium. "Non-transitory" means that the storage medium is a tangible device and does not contain a signal (e.g., electromagnetic wave), and this term includes a case in which data is semi-permanently stored in a storage medium and a case in which data is temporarily stored in a storage medium.

The method according to the various disclosed embodiments may be provided by being included in a computer program product. Computer program products may be traded between sellers and buyers as commodities. Computer program products are distributed in the form of a device-readable storage medium (e.g., compact disc read only memory (CD-ROM)), or are distributed directly or online (e.g., downloaded or uploaded) between two user devices (e.g., smartphones) through an application store (e.g., Play Store™). In the case of online distribution, at least a portion of the computer program product (e.g., downloadable app) may be temporarily stored or created temporarily in a device-readable storage medium such as the manufacturer's server, the application store's server, or the relay server's memory.

According to certain embodiments, each component (e.g., a module or a program) of the above-described components may include a singular or a plurality of entities, and some of the plurality of entities may be separately arranged in other components. According to certain embodiments, one or more components or operations among the above-described corresponding components may be omitted, or one or more other components or operations may be added. Alternatively or additionally, a plurality of components (e.g., a module or a program) may be integrated into one component. In this case, the integrated component may perform one or more functions of each component of the plurality of components identically or similarly to those performed by the corresponding component among the plurality of components prior to the integration. Operations performed by a module, a program module, or other elements according to certain embodiments of the present disclosure may be executed sequentially, in parallel, repeatedly, or in a heuristic method. Also, a portion of operations may be executed in different sequences, omitted, or other operations may be added.

The invention claimed is:

1. A wearable device, comprising:
a display;
a biosensor configured to detect biometric information of a user;
a communication circuitry configured to communicate with an external electronic device equipped with a gas sensor;
a distance sensor configured to detect distance information; and
a processor connected to the biosensor, display, and the communication circuitry, wherein the processor is configured to:
determine a distance to the external electronic device based on at least one of distance information via the distance sensor, and a signal strength of the external electronic device via the communication circuitry;
receive air quality information indicating a concentration of a harmful gas from the external electronic device through the communication circuitry,
estimate a concentration of the harmful gas at a user's location based on the determined distance to the external electronic device,
identify a dangerous situation based on the estimated concentration of harmful gas and blood oxygen saturation level indicated in the detected biometric information, and
control the display to display a notification message indicating the dangerous situation.

2. The wearable device of claim 1, wherein the processor is further configured to:
determine a content of the notification message based the estimated concentration of harmful gas, and the blood oxygen saturation level indicated in the biometric information.

3. The wearable device of claim 2, wherein the notification message is displayed based at least in part on an exposure time to the harmful gas.

4. The wearable device of claim 2, wherein the communication circuitry is further configured to communicate with a server, and
wherein the processor is further configured to:
control the communication circuitry to receive a plurality of pieces of air quality information obtained via a plurality of external electronic devices from the server,
determine the concentration of the harmful gas by applying a weight, respectively, to each of the plurality of pieces of air quality information.

5. The wearable device of claim 4, wherein the processor is configured to determine the weight based at least on a sensitivity constant of each of the plurality of external electronic devices.

6. The wearable device of claim 1, wherein the communication circuitry further comprises a Global Positioning System (GPS) receiver, and
wherein the processor is configured to determine a distance to the external electronic device based on location information determined via the GPS receiver.

7. The wearable device of claim 1, wherein the processor is further configured to:

control the biosensor to obtain the biometric information in response to a request for detecting the biometric information received from the external electronic device.

8. The wearable device of claim 1, wherein the communication circuitry is configured to communicate with a server, and wherein the processor is further configured to control the communication circuitry to transmit a sharing request to share the notification message regarding the dangerous situation with another external electronic device to the server.

9. A method in a wearable electronic device, comprising:
receiving, via communication circuitry, a transmission including air quality information indicating a concentration of harmful gas from an external electronic device equipped with a gas sensor;
detecting, via a biometric sensor of the wearable electronic device, biometric information indicating a blood oxygen saturation level of a user;
determining, via a distance sensor, a distance between the external electronic device and the wearable electronic device;
estimating a concentration of the harmful gas at a location of the wearable electronic device, based on the determined distance between the external electronic device and the wearable electronic device;
identifying, via at least one processor that is connected to the biometric sensor, a dangerous situation based on the estimated concentration of harmful gas and the blood oxygen saturation level; and
displaying a notification message indicating the identified dangerous situation through at least one of a display of the wearable electronic device, or the external electronic device, based on identification of the dangerous situation.

10. The method of claim 9, wherein displaying of the notification message further comprises determining content of the notification message based on the estimated concentration of harmful gas, and the blood oxygen saturation level contained in the biometric information.

11. The method of claim 10, wherein the display of the notification message is further based on at least a user's exposure time to the harmful gas.

12. The method of claim 10, wherein receiving the air quality information further comprises:
receiving a plurality of pieces of air quality information obtained via a plurality of external electronic devices from a server,
wherein the concentration of the harmful gas is determined by applying a weight, respectively, to each of the plurality of pieces of air quality information.

13. The method of claim 12, wherein the determination of the concentration of the harmful gas is based at least partly on a sensitivity constant of each of the plurality of external electronic devices.

* * * * *